United States Patent [19]

Peglion et al.

[11] Patent Number: 5,208,243
[45] Date of Patent: May 4, 1993

[54] 5-ISOQUINOLINESULFONAMIDES

[75] Inventors: Jean-Louis Peglion, Le Vesinet; Jean-Paul Vilaine, Chatenay Malabry; Nicole Villeneuve, Rueil Malmaison; Philip Janiak, Clichy, all of France

[73] Assignee: Adir et Compagnie, Courbevoie, France

[21] Appl. No.: 922,991

[22] Filed: Jul. 30, 1992

[30] Foreign Application Priority Data

Jul. 31, 1991 [FR] France ............... 91 09719

[51] Int. Cl.$^5$ .................. A61K 31/47; C07D 401/12
[52] U.S. Cl. .................... 514/309; 514/210; 514/212; 514/307; 540/597; 546/141; 546/146; 546/147; 546/149
[58] Field of Search ........... 546/141, 146, 147, 149; 514/307, 309, 210, 212; 540/597

[56] References Cited

U.S. PATENT DOCUMENTS 4,525,589  6/1985  Hidaka et al. ............ 546/149
5,081,246  1/1992  Hidaka et al. ............ 546/149

Primary Examiner—C. Warren Ivy
Assistant Examiner—James H. Turnipseed
Attorney, Agent, or Firm—Gordon W. Hueschen

[57] ABSTRACT

Compounds of formula (I):

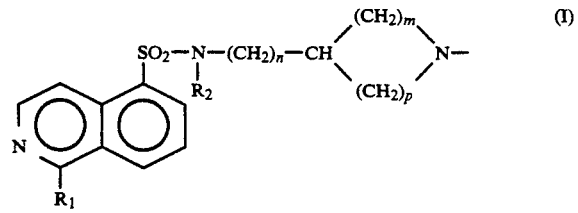

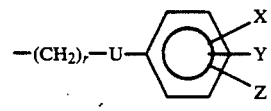

with $R_1$, $R_2$, U, X, Y, Z, n, m, p and r as defined in the description.

Medicinal products.

9 Claims, No Drawings

5-ISOQUINOLINESULFONAMIDES

The subject of the present invention is new 5-isoquinolinesulfonamides, a process for preparing them and pharmaceutical compositions containing them. It relates more particularly to the compounds of formula (I):

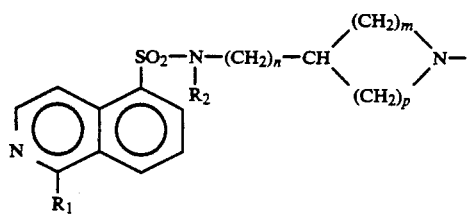

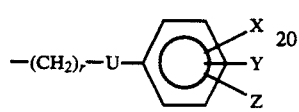

in which:
- n is 0 or an integer from 1 to 4,
- m and p are integers from 1 to 4,
- it being understood that the sum m+p is 2, 3, 4 or 5,
- r is an integer from 1 to 6,
- $R_H$ represents a hydrogen atom, a chlorine atom or a hydroxyl group,
- $R_2$ represents a hydrogen atom, a lower alkyl, lower alkenyl, lower alkynyl, cycloalkyl, lower cycloalkylalkyl, phenyl or lower phenylalkyl group,
- X, Y or Z, which are identical or different, represent a hydrogen atom, a halogen atom, or a group chosen from lower alkyl, lower alkoxy, nitro, amino, cyano, acetamido, carboxamido, or X and Y, or Y and Z, together form, with the 2 carbon atoms of the phenyl nucleus carrying them, a furan, dihydrofuran or benzene ring,
- U represents a single bond, an oxygen atom, a sulfur atom or a group chosen from: carbonyl, sulfinyl, sulfonyl, —NH—CO—, —CO—NH—, —O—(CH$_2$)$_r$—O— with r' meaning an integer equal to 2 or 3, —(CH$_2$)$_{r''}$—O— (CH$_2$)$_{r'''}$— with r'' and r''' meaning integers equal to 1 or 2, $$-\underset{R_3}{\overset{|}{N}}-$$

where
$R_3$ represents:
- a hydrogen atom,
- a formyl group,
- an —A, —CO—A or —CO—O—A group, with A meaning a lower alkyl, lower alkenyl, lower alkynyl, cycloalkyl or lower cycloalkylalkyl group,
- a —(CH$_2$)$_q$-phenyl group or a substituted —(CH$_2$)$_q$-phenyl group, with q meaning 0 or an integer from 1 to 4,
- a —CO—phenyl group or a substituted —CO-phenyl group,
- a —CO—O—phenyl group or a substituted —CO—O—phenyl group,
- a —CO—NR$_4$R$_5$ group
where $R_4$ and $R_5$: - which are identical or different, represent a hydrogen atom or a group chosen from lower alkyl, lower alkenyl, lower alkynyl, phenyl or lower phenylalkyl,
- or form with the nitrogen atom carrying them a saturated ring with 4 to 7 members, it being understood—that the term "substituted" which applies to the groups —(CH$_2$)$_q$—phenyl, —CO—phenyl or —CO—O—phenyl means that these groups may be substituted by one or more radicals chosen from: lower alkyl, lower alkoxy, hydroxyl, a halogen atom and trifluoromethyl, it being understood—that the terms "lower alkyl" and "lower alkoxy" mean linear or branched saturated carbon groups containing from 1 to 6 carbon atoms,
- that the terms "lower alkenyl" and "lower alkynyl" denote linear or branched unsaturated groups containing from 2 to 6 carbon atoms,
- that the term "cycloalkyl" denotes a saturated carbon ring containing from 3 to 8 members.

Compounds with an isoquinolinesulfonamide structure showing in particular an antiaggregation (JP 63-325910), vasodilatory (EP 109023), or bronchorelaxant (U.S. Pat. No. 4,857,301) activity are known from the literature.

The state of the prior art also consists of the following documents: JP 02073067, EP 187371 and EP 061673.

Substantial structural modifications led to the compounds of the present invention, which compounds exhibit a particularly potent and extensive pharmacological and therapeutic activity, which does not occur among the compounds of the prior art.

Indeed, the compounds of the present invention combine a remarkable myocardial and peripheral protecting effect with a very useful antivasoconstrictive activity.

These activities are confirmed by numerous studies both in vitro and in vivo (see examples of the pharmacological study 31 to 36).

The subject of the present invention is also the process for preparing the compounds of formula (I) wherein:
- an amine of formula (II):

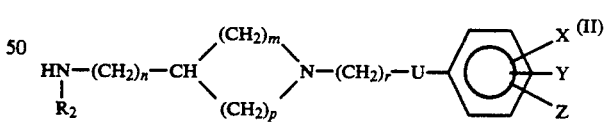

in which R$_2$, X, Y, Z, U, n, m, p, and r have the same meanings as in formula (I),
is condensed with a compound of formula (III):

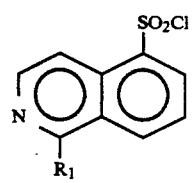

in which R$_1$ has the same meaning as in formula (I), to give a compound of formula (I):

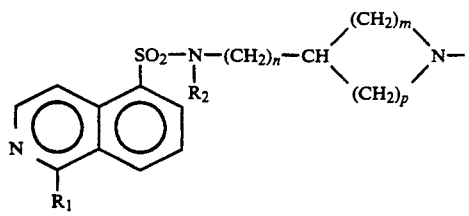

(I)

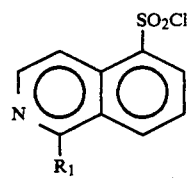

(III)

in which $R_1$ has the same meaning as in formula (I), to give a compound of formula (I/a):

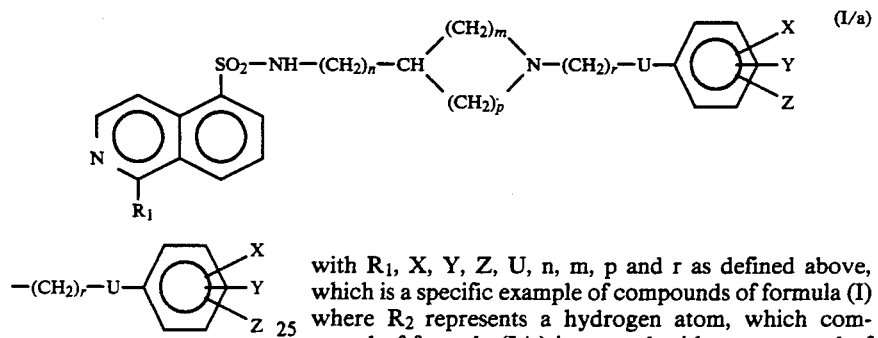

(I/a)

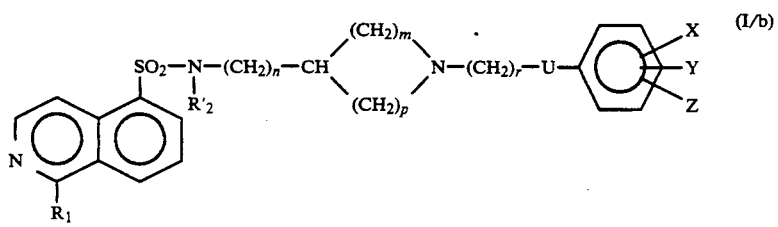

with $R_1$, $R_2$, X, Y, Z, U, n, m, p and r as defined above, whose isomers are separated where appropriate and which is salified, if desired, with a pharmaceutically acceptable acid, which compounds of formula (I) are purified if desired by a crystallization and/or chromatographic technique.

The present invention also relates to the process for preparing the compounds of formula (I) wherein:
- an amine of formula (II/a):

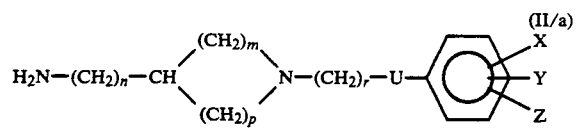

(II/a)

in which X, Y, Z, U, n, m, p and r have the same meanings as in general formula (I), is condensed with a compound of formula (III):

with $R_1$, X, Y, Z, U, n, m, p and r as defined above, which is a specific example of compounds of formula (I) where $R_2$ represents a hydrogen atom, which compound of formula (I/a) is reacted with a compound of formula $R'_2$-Hal with $R'_2$ representing a lower alkyl, lower alkenyl, lower alkynyl, cycloalkyl, lower cycloalkylalkyl, phenyl or lower phenylalkyl group, to give a compound of formula (I/b):

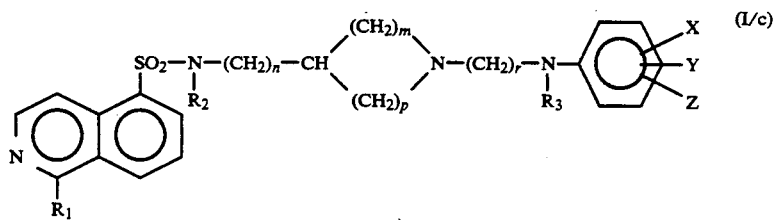

(I/b)

in which $R_1$, X, Y, Z, U, n, m, p, r and $R'_2$ are as defined above, which is a specific example of compounds of formula (I) where $R_2$ represents an $R'_2$ group.

The set of compounds of formula (I/a) and (I/b) form the set of compounds of formula (I).

The compounds of formula (I/a) and (I/b) may be separated where appropriate into their various isomers and salified, if desired, with a pharmaceutically acceptable acid.

The compounds of formula (I/a) and (I/b) may also be purified, if desired, by a crystallization and/or chromatographic technique.

The present invention also relates to a process for preparing compounds of formula (I/c):

(I/c)

in which $R_1$, $R_2$, $R_3$, X, Y, Z, n, m, p and r have the same meaning as in formula (I),
wherein

- an amine of formula (II/b):

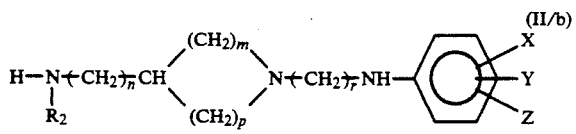

in which $R_2$, X, Y, Z, n, m, p and r are as defined above,
is condensed with a compound of formula (III),

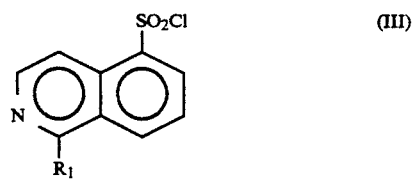

in which $R_1$ is as defined above,
to give a compound of formula (I/d):

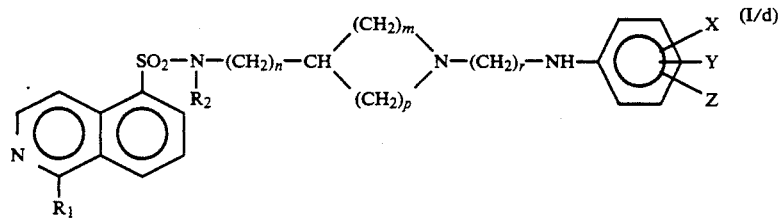

in which $R_1$, $R_2$, X, Y, Z, n, m, p and r are as defined above, which is a specific example of compounds of formula (I/c) where $R_3$ represents a hydrogen atom, which compound of formula (I/d) is substituted on the amine by a group of formula $R'_3$, where $R'_3$ has the same meaning as $R_3$ with the exception of the hydrogen atom, to give a compound of formula (I/e):

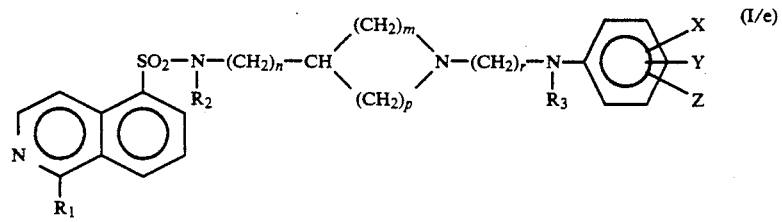

in which $R_1$, $R_2$, X, Y, Z, n, m, p, r and $R'_3$ are as defined above, the compounds of formula (I/d) and (I/e) forming the set of compounds of formula (I/c).

The compounds of formula (I/c) may be separated where appropriate into their various isomers and salified, if desired, with a pharmaceutically acceptable acid.

The compounds of formula (I/c) may also be purified, if desired, by a crystallization and/or chromatographic technique.

The raw materials used in the processes described above are either known products or products prepared from known substances according to processes described for preparing similar products as indicated in the following examples.

The compounds of formula (I) may be converted to addition salts with acids, which salts thereby form part of the invention. As acids which may be used for forming these salts, there may be mentioned, for example in the inorganic series, hydrochloric, hydrobromic, sulfuric and phosphoric acids, and in the organic series, acetic, propionic, maleic, fumaric, tartaric, nitric, oxalic, benzoic, methanesulfonic, isethionic and benzenesulfonic acids and the like.

On the other hand, if one or more asymmetric carbons exist, the compounds of formula (I) may exist in the form of diastereoisomers or enantiomers which thereby form part of the invention, in pure form or in the form of a mixture.

The compounds of formula (I) and the pharmaceutically acceptable addition salts thereof possess useful therapeutic properties, especially in the cardiovascular domain.

Pharmacological tests carried out in vitro have shown that the compounds of the invention have, in addition, an antivasoconstrictive activity with respect to the various types of mediators involving in particular the regulation of intracellular calcium, a myocardial-protecting activity with respect to a calcium excess, ischemia-reperfusion or hypoxiareoxygenation sequences.

The studies carried out in vivo confirm the anti-vasoconstrictive activity and the anti-ischemic activity of these compounds and reveal a substantial protective effect with respect to vascular lesions of a proliferative nature.

These properties therefore enable the compounds of the present invention to be used as a medicinal product, especially in the cardiovascular domain in the treatment and prevention of myocardial ischemia and its different clinical expressions such as angina pectoris and myocardial infarction, but also in the treatment of disorders of the heart rate, vascular spasm, high blood pressure, vascular diseases and cardiac insufficiency, and more generally in the treatment and prevention of disorders linked to arterial aging and atherosclerosis.

These compounds may also be administered for the prevention of vascular restenoses or thromboses after by-pass, vascular, especially coronary dilatation, or other forms of vascular repermeabilization. They may also be used in metabolic pathologies constituting a cardiovascular risk factor, such as obesity, diabetes and dyslipidemias.

Moreover, the intracellular calcium-regulating effect of these compounds endows them with a possible therapeutic use as anti-platelet aggregating and antithrombotic agents or relaxing agents for the various types of smooth muscles (other than the vascular types already mentioned): bronchial, digestive, urinary or uterine.

Furthermore, numerous situations of tissue pain, whether they are linked to aging, ischemia, inflammation or to cell proliferation, even of cancerous nature, may be treated or prevented by the products of the present invention.

The pharmaceutical compositions thus obtained are generally provided in a dosage form. They may for example take the form of tablets, sugared pills, gelatin capsules, suppositories, solutions to be injected or taken orally, and can be administered orally, rectally, intramuscularly or parenterally.

The dosage may vary especially according to the age and weight of the patient, the route of administration, the nature of the disease and the associated treatments and consists of 1 to 100 mg doses, taken once or several times daily.

The following examples illustrate the invention but do not imply any limitation thereto.

The melting points are determined with the Köfler (K) heating stage optionally under a microscope (MK). The 1H nuclear magnetic resonance spectra (NMR) were produced using tetramethylsilane (TMS) as internal standard. The chemical shifts are expressed in parts per million (ppm). The infrared spectra were determined in the form of a potassium bromide pellet containing about 1% of the product to be analyzed.

EXAMPLE 1

N-Methyl-N-{1-[4-(p fluorophenoxy)butyl]-4-piperidyl}-5-isoquinolinesulfonamide fumarate Stage A
1-Bromo-4-(p-fluorophenoxy)butane 0.5 mole of potassium hydroxide are dissolved in 200 cm³ of methanol. 0.5 mole of p-fluorophenol, 3.4 moles of 1,4-dibromobutane and 3 mmol of potassium iodide are added. The mixture is refluxed for 24 hours, with stirring.

After evaporation of the solvent, the residue is taken up in ether and washed with water and then with 1N sodium hydroxide. After removing the excess dibrominated compound, the compound is distilled by means of a Kughelrohr system.

An oil which is the expected compound is obtained: b.p.(1.33 Pa)=100° C.
Yield: 66%.

Stage B
N-Methyl-N-[1-(benzyl)-4-piperidyl]acetamide.

0.2 mole of acetyl chloride is slowly added to a solution containing 0.2 mole of N-[1-(benzyl)-4-piperidyl]-N-methylamine, 0.2 mole of triethylamine and 500 cm³ of methylene chloride. The mixture is left in contact for 2 hours, evaporated, taken up in ether and then washed with water. After evaporation, an oil which corresponds to the expected compound is obtained:
Yield: 80%.

Stage C
N-Methyl-N-(4-piperidyl)acetamide 0.38 mole of the compound obtained in stage B, in 700 cm³ of ethanol, is hydrogenated with 0.38 mole of acetic acid under a hydrogen pressure of 4910⁴ Pa, at 50° C. and in the presence of 2 grams of palladium hydroxide.

After filtration and evaporation, the residue is taken up in 500 cm³ of methylene chloride and then basified, with stirring and at low temperature, with 0.38 mole of 5N sodium hydroxide.

The mixture is decanted, dried and then evaporated. The expected compound is obtained.
Yield: 83%
Melting point: <50° C.

Stage D
N-Methyl-N-{1-[4-(p-fluorophenoxy)butyl]-4-piperidyl}acetamide.

A mixture containing 0.1 mole of the compound obtained in stage A, 0.1 mole of the compound obtained in stage C and 0.1 mole of potassium carbonate in 250 cm³ of acetone is heated to reflux.

It is maintained stirring for 12 hours. After evaporation, the residue is taken up with ether and then washed with water. The ethereal phase is extracted with 1N hydrochloric acid and the acidic phases are then basified at low temperature. The mixture is extracted with ether, dried and then evaporated. An oil which corresponds to the expected compound and which will then be used without intermediate purification is obtained.
Yield: 87%.

Stage E
N-{1-[4-(p-Fluorophenoxy)butyl]-4-piperidyl}-N-methylamine.

0.05 mole of the compound obtained in stage D is refluxed for 12 hours in the presence of 570 cm³ of methanol and 340 cm³ of 5N hydrochloric acid. The methanol is evaporated and the mixture is poured into ice and then basified with sodium hydroxide. It is extracted with ether.

After evaporation, an oil which corresponds to the expected compound is obtained. Yield: 89%.

Stage F
N-Methyl-N-{1-[4-(p-fluorophenoxy)butyl]4-piperidyl}5-isoquinolinesulfonamide.

0.1 mole of finely pulverized 5-isoquinoline sulfochloride hydrochloride is added, with stirring and at room temperature, to a solution of 0.1 mole of the compound obtained in stage E and 0.2 mole of diisopropylethylamine in 200 cm³ of methylene chloride.

The mixture is maintained stirring for 12 hours and then transferred into a flask. It is washed with 100 cm³ of 1N sodium hydroxide, dried and evaporated. The residual oil is chromatographed on 30 times its weight of silica (AMIKON 60Å), using as eluent a solution of methylene chloride/methanol (95/5), to give 12 grams of an oil which corresponds to the expected compound.

Stage G
The title compound.

12 grams of the oil obtained in stage F are converted to the fumarate salt by adding 2.9 grams of fumaric acid in solution in 155 cm³ of ethanol. 10.3 grams of the title compound are thus obtained.
Melting point: 144°-146° C.
Crystallization solvent: ethanol.

| Spectral characteristics |
| --- |
| Infrared: ν (NH/OH): 2800–2300 cm⁻¹ |
| ν (C=O): 1685 cm⁻¹ |
| 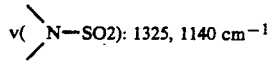 ν(N—SO2): 1325, 1140 cm⁻¹ |

NMR (D₂O)

1H: 9.45 ppm (singlet);      1H: 8.7 ppm (doublet);

-continued

Spectral characteristics

3H: 8.2–8.5 ppm (2 mulitplets);
4H: 6.85 ppm (2 multiplets);
2H: 3.9 ppm (triplet);
2H: 2.9 ppm (multiplet);
4H: 2.4 and 2.5 ppm (2 triplets);
2H: 1.25 ppm (multiplet);
OH and NH$^+$ proton not revealed.

1H: 7.85 ppm (triplet);
2H: 6.5 ppm (singlet);
1H: 3.8 ppm (multiplet);
3H: 2.7 ppm (singlet);
6H: 1.4–1.9 ppm (2 multiplets);

EXAMPLE 2

N-Methyl-N-{1-[4-(p-nitrophenoxy)butyl]-4-piperidyl}-5-isoquinolinesulfonamide fumarate The title compound is obtained in stage G by carrying out the procedure as in Example 1 but replacing, in stage A, p-fluorophenol with p-nitrophenol.
Yield: 32%.
Melting point: 156°–158° C.
Crystallization solvent: methanol.

EXAMPLE 3

N-Methyl-N-{1-[4-(phenoxy)butyl]4-piperidyl}-5 isoquinolinesulfonamide fumarate

The title compound is obtained in stage G by carrying out the procedure as in Example 1 but replacing, in stage A, p-fluorophenol with phenol.
Melting point: 176°–178° C.
Crystallization solvent: methanol.

EXAMPLE 4

N-Methyl N-{1-[4-(p-methylphenoxy)butyl]-4-piperidyl}-5-isoquinolinesultonamide fumarate The title compound is obtained in stage G by carrying out the procedure as in Example 1 but replacing, in stage A, p-fluorophenol with p-cresol.
Yield: 31%.
Melting point: 160°–163° C.
Crystallization solvent: ethanol.

EXAMPLE 5

N-Methyl-N-{1-4-(1-naphthyloxy)butyl]4-piperidyl}-5-isoquinolinesulfonamide fumarate The title compound is obtained in stage G by carrying out the procedure as in Example 1 but replacing, in stage A, p-fluorophenol with 1-naphthol.
Yield: 32%.
Melting point: 184°–186° C.
Crystallization solvent: ethanol.

EXAMPLE 6

N-Methyl-N-{1-[4-(p-chlorophenoxy)butyl-4-piperidyl}-5-isoquinolinesulfonamide hydrochloride The title compound is obtained by carrying out the procedure as in Example 1 but replacing, in stage A, p-fluorophenol with p-chlorophenol and by replacing, in stage G of Example 1, fumaric acid with hydrochloric acid.
Melting point: 194°–196° C.
Crystallization solvent: methanol.

EXAMPLES 7 TO 11

The following title compounds are successively obtained by following the procedure described in Example 6 but replacing, in stage A of Example 1, p-fluorophenol with appropriate compounds:

EXAMPLE 7

N-Methyl-N-{1-[4-(p-methoxyphenoxy)butyl]-4-piperidyl}-5-isoquinolinesulfonamide hydrochloride
Melting point: 176°–179° C.
Crystallization solvent: acetonitrile.

EXAMPLE 8

N-Methyl N-{1-[4-(p-cyanophenoxy)butyl]4-piperidyl}-5-isoquinolinesulfonamide dihydrochloride
Melting point: 224°–226° C.
Crystallization solvent: acetonitrile.

EXAMPLE 9

N-Methyl-N-{1-[4-(2,3-dihydrobenzofuran-5-yloxy)-butyl]-4-piperidyl}-5-isoquinolinesulfonamide dihydrochloride
Yield: 40%.
Melting point: 194°–197° C.
Crystallization solvent: ethanol.

EXAMPLE 10

N-Methyl-N-{1-[4-(m-fluorophenoxy)butyl]-4-piperidyl}-5-isoquinolinesulfonamide dihydrochloride
Melting point: 185°–186° C.
Crystallization solvent: acetonitrile.

EXAMPLE 11

N-Methyl-N-{1-4-(o-fluorophenoxy)butyl]-4-piperidyl}-5-isoquinolinesulfonamide dihydrochloride
Yield: 39.5%.
Melting point: 200°–203° C.
Crystallization solvent: acetonitrile.

EXAMPLE 12

N-Methyl-N-{1-[4-(p-fluorophenylthio)butyl]-4-piperidyl}-5-isoquinolinesulfonamide dihydrochloride The title compound is obtained by carrying out the procedure as in Example 1 but replacing, in stage A, p-fluorophenol with 4-fluorothiophenol and by replacing, in stage F, fumaric acid with hydrochloric acid.
Melting point: 145° C.
Crystallization solvent: ethyl acetate.

EXAMPLE 13

N-{1-[4-(p-fluorophenoxy)butyl]4-piperidyl)}-5-isoquinolinesulfonamide dihydrochloride The title compound is obtained by carrying out the procedure as in Example 1 but replacing, in stage B, N-[1-(benzyl)-4-piperidyl]-N-methylamine with 1-benzyl- 4-aminopiperidine and by replacing, in stage G, fumaric acid with hydrochloric acid.
Melting point: 160° C.
Crystallization solvent: acetonitrile.

EXAMPLE 14

N-{1-[5-(p-fluorophenoxy)pentyl]-4-piperidyl}-5-isoquinolinesulfonamide

The following are successively obtained by carrying out the procedure as in Example 1 but replacing, in stage A, 1,4-dibromobutane with 1,5-dibromopentane and, in stage B, N-[1-(benzyl)-4-piperidyl]-N-methylamine with 1-benzyl-4-aminopiperidine:

Stage A
1-Bromo-5-(p-fluorophenoxy)pentane.
  Yield: 49%.
  b.p.(10.66 Pa)=120° C.

Stage B
N-[1-(Benzyl)-4-piperidyl]acetamide.

Stage C
N-(4-piperidyl)acetamide.

Stage D
N-{1-[5-(p-Fluorophenoxy)pentyl]-4-piperidyl}acetamide.
  Yield: 48%.
  Melting point: 133°-134° C.

Stage E
4-Amino-1-[5-(p-fluorophenoxy)pentyl]piperidine.
  Yield: 65%.

Stage F
Title compound.
  Melting point: 142°-145° C.
  Crystallization solvent: acetonitrile.

| Spectral characteristics | | |
|---|---|---|
| Infrared: | ν (NH): | 3309 cm$^{-1}$ |
| | ν (NH—SO$_2$): | 1321, 1215 cm$^{-1}$ |
| NMR (CDCl$_3$): | | |
| 1H: 9.35 ppm (singlet); | | 1H: 8.7 ppm (doublet); |
| 2H: 8.45 ppm (2 doublets); | | 1H: 8.2 ppm (doublet); |
| 1H: 7.7 ppm (triplet); | | 2H: 6.95 ppm (multiplet); |
| 2H: 6.75 ppm (multiplet); | | 1H exchangeable: 5.1 ppm (multiplet); |
| 2H: 3.85 ppm (triplet); | | |
| 2H: 2.7 ppm (doublet); | | 1H: 3.15 ppm (multiplet); |
| 2H: 1.95 ppm (triplet); | | 2H: 2.25 ppm (triplet); |
| 6H: 1.4 ppm (multiplet); | | 4H: 1.7 ppm (multiplet); |

EXAMPLE 15

N-{[1-[3-(p-Fluorophenoxy)propyl]-4-piperidyl]methyl}-5-isoquinolinesulfonamide

Stage A
1-Bromo-3-(p-fluorophenoxy)propane.

The expected compound is obtained by carrying out the procedure as in stage A of Example 1 but replacing 1,4-dibromobutane with 1,3-dibromopropane.
  Yield: 43%.
  b.p.(1.33 Pa)=85° C.

Stage B
{1-[3-(p-Fluorophenoxy)propyl]-4-piperidyl}carboxamide.

46.2 grams of the compound obtained in stage A and 25.6 grams of isonipecotamide are dissolved in 560 cm3 of acetone in the presence of 27.6 grams of potassium carbonate. The mixture is refluxed for 12 hours, with stirring. It is evaporated, taken up in ether and then washed with water. The ethereal phase is extracted with 1N hydrochloric acid and the aqueous phases are then basified at low temperature. The precipitated is filtered and dried. The desired compound is obtained.
  Melting point: 140°-142° C.

Stage C
4-Aminomethyl-1-[3-(p-Fluorophenoxy)propyl]piperidine.

3.8 grams of lithium aluminum hydride are added through a solids funnel to a suspension of 26 grams of the compound obtained in stage B. The mixture is refluxed for 2 hours. The reaction medium is decomposed using 2.6 cm$^3$ of water and then 2.1 cm$^3$ of sodium hydroxide and finally 9.6 cm$^3$ of water, filtered and the filtrate is then evaporated. 13.1 grams of an oil are obtained which corresponds to the expected compound and which may be used without further purification.

Stage D
Title compound.

13 grams of 5-isoquinoline sulfochloride hydrochloride are added, in fractions and with stirring at room temperature, to a mixture of 13 grams of the compound obtained in stage C and 17.8 cm$^3$ of diisopropylethylamine in 500 cm$^3$ of methylene chloride. The mixture is maintained stirring for 12 hours. It is transferred into a separating funnel and then washed with 50 cm$^3$ of 1N sodium hydroxide, dried and evaporated. The residue is chromatographed on silica using a methylene chloride/methanol mixture (95/5) as eluent. The oil obtained is thickened using acetonitrile. 4.5 grams of the title compound are obtained.
  Melting point: 123°-125° C.
  Crystallization solvent: acetonitrile.

EXAMPLE 16

N-Methyl-N-{2-[1-[2-(p-fluorophenoxy]ethyl]-4-piperidyl]ethyl}-5-isoquinolinesulfonamide The title compound is prepared by following a procedure similar to that of Example 15 but replacing, in stage C, 4-aminomethyl-1-[3-(p-fluorophenoxy)propyl]-piperidine with 4-[2-(amino)ethyl]-1-[2-(p-fluorophenoxy)ethyl]piperidine.

EXAMPLE 17

N-Methyl-N-{[1-[3-(p-fluorophenoxy)propyl]-4-piperidyl]methyl}-5-isoquinolinesulfonamide dihydrochloride Stage A
N-Methyl-N-{[1-[3-(p-fluorophenoxy)propyl]-4-piperidyl]methyl}-5-isoquinolinesulfonamide.

A suspension of 6 grams of the compound of Example 15 in 30 cm$^3$ of dimethylacetamide is poured into a suspension of 0.6 g of 60% sodium hydride in 20 cm$^3$ of dimethylacetamide. 1.8 g of methyl iodide are added and the mixture is allowed to stand for 12 hours at room temperature. It is diluted with water, extracted with ethyl acetate and dried. It is purified by chromatography on silica using a methylene chloride/methanol mixture (95/5) as eluent.

5.5 g of an oil which corresponds to the expected compound are obtained.

Stage B
Title compound.

5.5 g of the compound obtained in stage A is taken up in 10 cm$^3$ of acetonitrile. 7.5 cm$^3$ of a 3.3N solution of hydrochloric ether are added to this solution. 3.1 g of a solid which corresponds to the title compound are obtained.
  Melting point: 146°-149° C.
  Crystallization solvent: acetonitrile.

| Spectral characteristics | |
|---|---|
| Infrared: ν (NH$^+$): | 2515 cm$^{-1}$ |
| NMR (DMSO-d$_6$) | |
| 1H: 9.55 ppm (singlet); | 1H: 8.75 ppm (doublet); |
| 1H: 8.5 ppm (doublet); | 2H: 8.45 ppm (multiplet); |
| 1H: 7.9 ppm (triplet); | 2H: 7.15 ppm (triplet); |
| 2H: 6.95 ppm (multiplet); | 2H: 4.05 ppm (triplet + multiplet); |
| 11H: 3.6–2.8 ppm | |

-continued

7H: 2.2–1.3 ppm

EXAMPLE 18

N-{[1-[3 (Phenoxy)propyl]-4-piperidyl]methyl}-5-isoquinolinesulfonamide

The title compound is obtained in stage D by carrying out the procedure as in Example 15 but replacing, in stage A, p-fluorophenol with phenol.

Yield: 39%.

EXAMPLE 19

N-Methyl-N-{[1-[3-(phenoxy)propyl]-4-piperidyl]methyl}-5-isoquinolinesufonamide

The title product is obtained by carrying out the procedure as in stage A of Example 17 but replacing the compound of Example 15 with the compound of Example 18.

Melting point: 99°–101° C.

Crystallization solvent: cyclohexane.

EXAMPLE 20

N-Methyl-N-{[1-[4-(p-fluorophenyl)butyl]-4-piperidyl]methyl}-5-isoquinolinesulfonamide dihydrochloride Stage A Ethyl [1-[4-(p-fluorophenyl)butyl]-4-piperidyl}carboxylate.

The expected compound is obtained by carrying out the procedure as in stage B of Example 15 but replacing isonipecotamide with ethyl isonipecotate and the compound of stage A with 4-fluorophenyl-1-iodobutane.

Stage B

{1-[4-(p-Fluorophenyl)butyl]-4-piperidyl}-N-methylcarboxamide

The compound obtained in the preceding stage is saponified before being dissolved in methylene chloride. It is treated with carbonyldiimidazole and after a contact time of 1 hour (end of gaseous emission), a solution of methylamine is poured into methylene chloride while maintaining the stoichiometry. The mixture is left in contact overnight, washed with water, dried and the solvent evaporated.

Stage C

1-[4-(p-Fluorophenyl)butyl]-4-[(methylamino)methyl]-piperidine.

The compound of the preceding stage is reduced by the action of lithium aluminum hydride according to a procedure which is identical to that of stage C of Example 15.

Stage D

Title compound

The desired compound is obtained by using a procedure identical to that of stages F and G of Example 1 but replacing, in stage F, the compound of stage E of Example 1 with the compound of the preceding stage and, in stage G of Example 1, fumaric acid with hydrochloric acid.

Yield: 32%.

Melting point: 182° C.

Crystallization solvent: ethyl acetate.

EXAMPLE 21

N-Methyl-N-{[1-[4-(p-fluorophenoxy)butyl]-3-pyrrolidinyl]methyl}-5-isoquinolinesulfonamide dihydrochloride Stage A N-Methyl-(1-benzyl-2-oxo-4-pyrrolidinyl)carboxamide.

0.2 mole of (1-benzyl-2-oxo-4-pyrrolidinyl)carboxylic acid (described in Journal of Organic Chemistry, 1961; 26: p 1519) is dissolved in 200 cm$^3$ of methylene chloride. The mixture is treated with 32.4 g of carbonyldiimidazole. It is left in contact for 1 hour and then a solution consisting of 20 g of methylamine and 200 cm$^3$ of methylene chloride is added. The mixture is left in contact for 12 hours at room temperature, washed with water and then dried over magnesium sulfate. An oil which is the expected compound is obtained.

Yield: 92%.

Stage B

N-{[1-(Benzyl)-3-pyrrolidinyl]methyl}-N-methylamine 40 g of the compound obtained in stage A is reduced by means of 13.1 g of lithium and aluminum hydride.

33.6 g of the compound of stage B are obtained in an oily form.

Yield: 89%.

Stage C

N-Methyl-N-{[1-(benzyl)-3-pyrrolidinyl]methyl}acetamide.

33.6 g of the compound obtained in stage B are dissolved in 350 cm$^3$ of methylene chloride and 21.6 cm$^3$ of triethylamine. The mixture is acetylated using 10.9 cm$^3$ of acetyl chloride. It is left in contact for 2 h, evaporated and taken up in ether, washed with water and then dried. The oil obtained after evaporation is chromatographed on silica using the methylene chloride/methanol mixture (95.5) as eluent.

12.5 g of the desired compound are obtained.

Stage D

N-Methyl-N-[(3-pyrrolidinyl)methyl]acetamide acetate.

0.05 mole of the compound obtained in stage C in 130 cm$^3$ of ethanol and 3 cm$^3$ of acetic acid is hydrogenated in the presence of 1.3 g of palladium dihydroxide at 50° C. and at a pressure of 5 kilograms/cm$^2$. The mixture is evaporated and then filtered. 12 g of the expected compound are obtained.

Stage E

N-Methyl-N-{[1-[4-(p-fluorophenoxy)butyl]-3-pyrrolidinyl]methyl}acetamide.

The desired compound is obtained by carrying out the procedure as in stage D of Example 1 but replacing the compound of stage C with the compound obtained in stage D of Example 21.

Yield: 38%.

Stage F

N-{[1-[4-(p-fluorophenoxy)butyl]-3-pyrrolidinyl]methyl}-N-methylamine.

8.5 g of the compound obtained in stage E are refluxed for 20 hours in the presence of 80 cm$^3$ of concentrated hydrochloric acid, 80 cm$^3$ of water and 260 cm$^3$ of methanol. The mixture is evaporated, poured onto ice, basified with sodium hydroxide and then extracted with ether. The desired compound is obtained in the form of an oil after evaporation.

Yield: 78%.

Stage G

Title compound

The title product is obtained by carrying out the procedure in a manner similar to stages F and G of Example 1 but using the compound obtained in the preceding stage and using hydrochloric ether instead of fumaric acid.

Yield: 28%.

EXAMPLE 22

N-Methyl-N-{[1-[3-(p-fluorophenoxy)propyl]-3-pyrrolidinyl]methyl}-5-isoquinolinesulfonamide dihydrochloride The title compound is obtained by carrying out the procedure as in Example 21 but replacing, in stage E, 1-bromo-4-(p-fluorophenoxy)butane with 1-bromo- 3-(p-fluorophenoxy)propane.

Yield: 51%.
Melting point: 145° C.
Crystallization solvent: ethyl acetate.

| Spectral characteristics | | |
|---|---|---|
| Infrared: | $\nu$ (OH): | 3400 cm$^{-1}$ |
| | $\nu$ (NH$^+$): | 2800–1800 cm$^{-1}$ |
| | $\nu$ (NH—SO2): | 1377, 1142 cm$^{-1}$ |

EXAMPLE 23

N-Methyl-N-{1-[5-(p-fluorophenoxy)-3-oxapentyl]-4-piperidyl}-5-isoquinolinesulfonamide dihydrochloride Stage A
1-Chloro-5-(p-fluorophenoxy)-3-oxapentane.

The desired product is obtained by carrying out the procedure as in stage A of Example 1 but replacing 1,4-dibromobutane with 1,5-dichloro-3-oxapentane.

Yield: 53%.

Stage B
5-(p-Fuorophenoxy)-1-iodo-3-oxapentane.

A mixture of 0.1 mole of the compound obtained in stage A and 0.12 mole of sodium iodide in 100 cm$^3$ of methyl ethyl ketone is refluxed for 24 hours. The solvent is evaporated, the residue taken up in ether, washed with water and then with 1N sodium thiosulfate, dried and then evaporated. The expected compound is obtained in an oily form.

Yield: 90%.

Stage C
Title compound.

The title compound is obtained by carrying out the procedure in a manner similar to stages D to G of Example 1 but using, in place of the compound of stage A of Example 1, the compound of stage B above and replacing, in stage G of Example 1, fumaric acid with hydrochloric ether.

Yield: 47%.
Melting point: 210°–212° C.
Crystallization solvent: acetonitrile.

EXAMPLE 24

N-{[1-[3-(p-fluorophenylamino)propyl]-4-piperidyl]methyl}-5-isoquinolinesulfonamide fumarate Stage A
1 Bromo-2-(fluorophenylaminocarbonyl)ethane.

A solution of 0.1 mole of p-fluoroaniline, 14 cm$^3$ of triethylamine and 100 cm$^3$ of benzene is prepared. A mixture of 17.1 g of 3-bromopropionic acid chloride and 20 cm$^3$ of benzene are added dropwise and at room temperature. The mixture is left in contact for 12 h, with stirring, and then transferred into a separating funnel. It is dried and then evaporated to give 21 g of the expected compound.

Melting point: 136°–138° C.

Stage B
{1-[2-(p-Fluorophenylaminocarbonyl)ethyl]-4 piperidyl}carboxamide.

The desired compound is obtained by carrying out the procedure as in stage B of Example 15 but replacing the compound obtained in stage A of Example 15 with the compound obtained in stage A above.

Yield: 38%.

Stage C
4-Aminomethyl-1-[3-(p-fluorophenylamino)propyl]-piperidine.

9.5 g of the compound obtained in the preceding stage is suspended in 300 cm$^3$ of tetrahydrofuran. 0.064 mole of lithium aluminum hydride is introduced through a solids funnel. A further 100 cm$^3$ of tetrahydrofuran are added and the mixture is refluxed for 12 hours. After treating the reaction medium, 5.5 g of an oil corresponding to the desired compound are obtained.

Yield: 65%.

Stage D
Title compound.

The title compound is obtained by carrying out the procedure as in stage D of Example 15 and after salification with fumaric acid in ethanol.

Melting point: 168°–170° C.
Crystallization solvent: acetonitrile.

EXAMPLE 25

N-Methyl-N-{1-[3-(p-fluorophenylamino)propyl]-4-piperidyl]methyl}-5-isoquinolinesulfonamide fumarate Stage A
4-Ethoxycarbonyl-1-{[3-(p-fluorophenylamino)-3-oxo]-propyl}piperidine.

24.6 g of the compound obtained in stage A of Example 24 and 15.7 g of ethyl isonipecotate are dissolved in 360 cm$^3$ of acetone in the presence of 13.8 g of potassium carbonate. The procedure is then carried out in a manner similar to that of stage B of Example 16 to give the desired product.

Yield: 56%.

Stage B
{1-[3-(p-Fluorophenylamino)-3-oxopropyl]-4-piperidyl}-N-methylcarboxamide.

92 g of the compound obtained in stage A, saponified beforehand, is suspended in 500 cm$^3$ of methylene chloride. 0.313 mole of carbonyldiimidazole is added all at once. The mixture is left in contact for 2 h during which a progressive dissolution is observed. A solution of 33 g of methylaine in 400 cm$^3$ of methylene chloride is then added dropwise. After leaving in contact for 48 h, the mixture is transferred into a separating funnel and then washed with water. It is concentrated by half and then the precipitate which corresponds to the expected compound is filtered.

Yield: 46%.

Stage C
Title compound.

The title compound is obtained by carrying out the procedure as in stages C and D of Example 24 but using the compound obtained in stage B above.

Melting point: 174°–176° C.
Crystallization solvent: methanol.

EXAMPLE 26

N-Ethyl-N-{1-[4-(p-fluorophenoxy)butyl]-4-piperidyl}-5-isoquinolinesulfonamide dihydrochloride The title compound is obtained, after salification with fumaric acid in ethanol, by carrying out the procedure as in stage A of Example 17 but replacing the compound of Example 15 with the compound of Example 13 and methyl iodide with ethyl iodide.

Yield: 32.5%.
Melting point: 154°–156° C.
Crystallization solvent: acetonitrile.

EXAMPLE 27

N-Methyl-N-{[1-[3-(N-acetyl-p-fluorophenylamino)-propyl]-4-piperidyl]methyl}-5-isoquinolinesulfonamide dihydrochloride 0.01 mole of the compound obtained in Example 25 and 0.011 mole of acetic anhydride are dissolved in 10 cm³ of acetic acid. The mixture is refluxed for 3 hours, with stirring. It is poured into 150 cm³ of water and then basified with 20% sodium hydroxide. The mixture is extracted with methylene chloride, dried and then evaporated. The oil obtained is dissolved in 10 cm³ of ethyl acetate and salified with hydrochloric ether. The mixture is precipitated and then filtered.

The title compound is obtained.
Yield: 27%.
Melting point: 135° C.
Crystallization solvent: ethyl acetate.

EXAMPLE 28

N-Methyl-N-{[1-[3-(N-formyl-p-fluorophenylamino)-propyl]-4-piperidyl]methyl}-5-isoquinolinesulfonamide hydrochloride 4.6 g of the compound obtained in Example 25, heated to 40° C. beforehand, are dissolved in 24.6 cm³ of 88% formic acid. 8.8 cm³ of acetic anhydride are added. The mixture is left in contact for 48 h. It is poured onto ice, basified and then extracted with ethyl acetate. After chromatography on silica using a methylene chloride/methanol mixture (95/5) as eluent, it is evaporated and taken up in 20 cm³ of ethyl acetate. 2.2 cm³ of 3N hydrochloric ether are then added. The mixture is cooled and the precipitate which corresponds to the expected compound is then filtered.

Melting point: 176°–178° C.
Crystallization solvent: ethyl acetate.

EXAMPLES 29 TO 34

By carrying out the procedure by analogy with the methods described above, the products of Examples 29 to 34 below are prepared:

EXAMPLE 29

N-Methyl-N-{[1-[3-(N-(ethoxycarbonyl)-p-fluorophenylamino)propyl]-4-piperidyl]methyl}-5-isoquinolinesulfonamide dihydrochloride

EXAMPLE 30

N-Methyl-N-{[1-[3-(N-(aminocarbonyl)-p-fluorophenyl-amino)propyl]-4-piperidyl]methyl}-5-isoquinolinesulfonamide hydrochloride

EXAMPLE 31

N-{1-[3-(N-p-Fluorophenyl-N-methylamino)propyl]-4-piperidylmethyl}-5-isoquinolinesulfonamide dihydrochloride m.p. (K): 158° C.

EXAMPLE 32

N-Methyl-N-{1-[3-(p-fluorophenylcarbonyl)propyl]-4-piperidylmethyl}-5-isoquinolinesulfonamide m.p. (MK): 118°–120° C.

EXAMPLE 33

N-Methyl-N-{1-[3-(N-p-fluorophenyl-N-methylamino)-propyl]-4-piperidylmethyl}-5-isoquinolinesulfonamide dihydrochloride m.p. (K): 225°–227° C.

EXAMPLE 34

N-{2-[1-[2-(p-fluorophenoxy)ethyl]-4-piperidyl]ethyl}-5-isoquinolinesulfonamide dihydrochloride m.p. (K): 158°–160° C.

EXAMPLE 35

Pharmacological study of the compounds of the invention

The very useful pharmacological and therapeutic properties of the compounds of the invention are revealed by numerous pharmacological tests. These tests will be presented in the following order:

| I  | In vitro studies of the compounds of the invention |
|----|-------------------------------------------------|
|    | A/ antivasoconstrictive activity |
|    | B/ myocardial-protecting effect |
| II | In vivo studies of the compounds of the invention |
|    | A/ effect on the cardiovascular reactivity |
|    | B/ study of the hemodynamic action |
|    | C/ effect on reperfusion arrhythmias |
|    | D/ effect on the proliferation rate after endothelial denudation. |

I IN VITRO STUDIES OF THE COMPOUNDS OF THE INVENTION

A/ antivasoconstrictive activity

Materials and methods

Studies are carried out on rings, 3 mm in length,
- of aortas removed from WISTAR rats (325–375 g) anesthetized with sodium pentobarbital (30 mg/kg intraperitoneally)
- of aortas, mesenteric arteries and iliac arteries removed from New Zealand rabbits (1.8–2 kg), also anesthetized with sodium pentobarbital (30 mg/kg intraperitoneally)

- or of coronary arteries from pigs anesthetized with nesdonal (8 mg/kg intravenously).

tion of rat aortas induced by a hyperpotassium medium.

TABLE (T1)

| CONCENTRATION INHIBITING BY 50% ($IC_{50}$) THE CONTRACTION OF RAT AORTAS INDUCED BY POTASSIUM DEPOLARIZATION | | | | | | | | |
|---|---|---|---|---|---|---|---|---|
| No of the tested example | 1 | 2 | 3 | 6 | 7 | 8 | 12 | 13 |
| $IC_{50}$ (in M) | $8.5 \times 10^{-7}$ | $1.3 \times 10^{-6}$ | $1.7 \times 10^{-6}$ | $1.1 \times 10^{-6}$ | $1.9 \times 10^{-6}$ | $9.5 \times 10^{-7}$ | $1.3 \times 10^{-6}$ | $2.9 \times 10^{-6}$ |
| No of the tested example | 15 | 17 | 19 | 21 | 22 | 24 | 25 | 26 |
| $IC_{50}$ (in M) | $3.5 \times 10^{-6}$ | $1.5 \times 10^{-6}$ | $2.8 \times 10^{-6}$ | $1.9 \times 10^{-6}$ | $3.6 \times 10^{-6}$ | $4.5 \times 10^{-6}$ | $3.1 \times 10^{-6}$ | $5.3 \times 10^{-6}$ |

The vascular rings are immersed in a normal physiological solution or in a physiological solution lacking calcium (+0.2 mM of the chelating agent EGTA), which is thermostatically regulated at 37° C. and aerated with a 95% $O_2$+5% $CO_2$ mixture. The rings are linked to a STATHAM tension sensor (UC2-GOULD). The optimal tension for each vessel is applied and a stabilization period of 90 min is observed for the preparations.

a) Antivasoconstrictive activity of the compounds of the invention in a physiological medium.

Study procedure

- The relaxant activity of the compounds of the invention, which were tested in cumulative concentrations added every 15 minutes, towards the contraction of vascular rings induced by a hyperpotassium medium (80 mM KCl, 37 mM NaCl), noradrenaline ($10^{-6}$ M), endothelin ($610^{-9}$ M) or a phorbol ester (TPA/phorbol 12 myristate- 13 acetate at $10^{-5}$ M), enabled the $IC_{50}$ (molar concentration which inhibits 50% of the maximum contraction) to be calculated.
- The activity of the compounds of the invention, preincubated for 15 minutes, is also evaluated by the limitation of vascular contraction induced by PDGF (Platelet Derived Growth Factor) at $310^{-11}$ M, by acetylcholine ($310^{-8}$ to $310^{-5}$ M) or by sequences of electrical stimulation.

Results

Table (T1) collates the $IC_{50}$ values obtained with the compounds taken as representative examples of the compounds of the invention with respect to the contraction of rat aortas induced by a hyperpotassium medium.

Tables (T2) and (T3) show the activity of the compounds of Examples 1 and 17 which are representative of the compounds of the invention with respect to the other vasoconstrictive stimuli tested.

(T2)

| ANTIVASOCONSTRICTIVE ACTIVITY OF THE COMPOUNDS OF THE INVENTION IN A NORMAL PHYSIOLOGICAL MEDIUM | | | |
|---|---|---|---|
| STIMULUS | VESSEL | COMPOUND OF EXAMPLE 1 $IC_{50}$ (M) | COMPOUND OF EXAMPLE 17 $IC_{50}$ (M) |
| Noradrenaline | rabbit aorta | $1.4 \times 10^{-6}$ | $1.5 \times 10^{-6}$ |
| Electrical stimulation | rabbit mesenteric artery | $4.0 \times 10^{-7}$ | $1.0 \times 10^{-7}$ |
| Endothelin | rabbit aorta | $8.1 \times 10^{-6}$ | $3.3 \times 10^{-6}$ |
| Phorbol ester | rabbit aorta | $3.0 \times 10^{-4}$ | $2.1 \times 10^{-5}$ |

(T3)

| | | % INHIBITION OF THE CONTRACTION AT $10^{-5}$ M | |
|---|---|---|---|
| STIMULUS | VESSEL | COMPOUND OF EXAMPLE 1 | COMPOUND OF EXAMPLE 17 |
| PDGF | Rabbit aorta | 20 | 30 |
| Acetylcholine | pig coronary artery | 61 | 64 | b) Antivasoconstrictive activity of the compounds of the invention in a medium without calcium.

Study procedures

The inhibitory effect of a concentration of the compounds of the invention, incubated for 30 minutes, towards a vascular contraction induced by noradrenaline ($10^{-6}$ M), angiotensin ($10^{-5}$ M), endothelin ($310^{-8}$ M) or caffeine (10 mM) in a medium lacking calcium, is tested.

Results

Table (T4) shows the activity of the compounds towards the contraction of rabbit aortas induced by noradrenaline in a medium lacking calcium.

(T4)

| % INHIBITION OF THE CONTRACTION INDUCED BY NORADRENALINE IN A MEDIUM WITHOUT CALCIUM | | |
|---|---|---|
| No of the example tested | Concentration of the compound | |
| | $10^{-6}$ M | $10^{-7}$ M |
| 1 | 61 | |
| 2 | 12 | |
| 3 | 47 | |
| 6 | 18 | |
| 7 | 13 | |
| 12 | 19 | |
| 13 | 42 | |
| 15 | 59 | |

(T4)-continued

% INHIBITION OF THE CONTRACTION INDUCED BY
NORADRENALINE IN A MEDIUM WITHOUT CALCIUM

| No of the example tested | Concentration of the compound | |
|---|---|---|
| | $10^{-6}$ M | $10^{-7}$ M |
| 17 | 90 | 40 |
| 19 | 67 | 31 |
| 21 | 73 | 17 |
| 22 | 82 | 43 |
| 24 | 67 | 38 |
| 25 | 77 | 22 |
| 26 | 26 | |

Table (T5) shows the activity of the compounds of Examples 1 and 17, which are representative of the compounds of the present invention, towards the other vasoconstrictive stimuli also tested in a medium lacking calcium.

(T5)

| | | % INHIBITION OF THE CONTRACTION AT $10^{-5}$ M | |
|---|---|---|---|
| STIMULUS | VESSEL | COMPOUND OF EXAMPLE 1 | COMPOUND OF EXAMPLE 17 |
| Angiotensin II | Rabbit aorta | 40 | 21 |
| Endothelin | Rabbit aorta | 42 | 67 |
| Phorbol ester | Rabbit aorta | 66 | 35 |
| Caffeine | Rabbit iliac artery | 30 | 63 |

CONCLUSION

The compounds of the invention exert a remarkable inhibitory activity towards the vascular contraction induced by various types of vasoconstrictive mediators (such as: noradrenaline, angiotensin II, acetylcholine, endothelin) or by a growth factor (such as PDGF) which involve, especially in a smooth muscle cell, the entry of calcium and the mobilization of intracellular calcium. These products very advantageously retain their activity in the absence of extracellular calcium. Furthermore, they are active in tests directly involving the activation of protein kinase C (phorbol ester) or the mobilization of intracellular calcium (caffeine).

B/ Study of the protective activity of the compounds of the invention on the myocardium a) Effect of the compounds of the invention on the intoxication of guinea pig left auricle.

Study procedure

The left auricles are removed from guinea pigs (350–450 g) anesthetized with sodium pentobarbital (30 mg/kg). The auricles are attached to a STATHAM tension sensor (UC2-GOULD) and the initial tension applied is 0.5 grams.

The auricles are electrically stimulated at 1 Hz by means of platinum electrodes. The intoxications are produced either by the addition of ouabain ($10^{-6}$ M) or by the addition of veratridine ($10^{-5}$ M). The test compounds are added 15 minutes before adding the toxic agent.

The results are presented in Tables (T6) and (T7).

(T6)

| EFFECT OF THE COMPOUNDS OF THE INVENTION ON AN OUABAIN INTOXICATION OF GUINEA PIG LEFT AURICLE | | | |
|---|---|---|---|
| | SOLVENT | COMPOUND OF EXAMPLE 1 $10^{-6}$ M | COMPOUND OF EXAMPLE 17 $10^{-5}$ M |
| % CONTRACTION | | | |
| 10 MIN | 201 ± 17.9 | 192 ± 29 | 201.5 ± 31.5 |
| 30 MIN | 63.7 ± 15 | 187.5 ± 30 | 186.5 ± 46 |
| 60 MIN | 45 ± 10 | 148.3 ± 33 | 179 ± 44 |
| CONTRACTURE (%) | | | |
| 15 MIN | 13.2 ± 7.7 | 0 | 0 |
| 30 MIN | 57.8 ± 13.7 | 1.9 ± 1.9 | 2.5 ± 2.5 |
| 60 MIN | 75 ± 12 | 18 ± 7 | 5 ± 3.3 |

(T7)

| EFFECT OF THE COMPOUNDS OF THE INVENTION ON A VERATRIDINE INTOXICATION OF GUINEA PIG LEFT AURICLE | | | |
|---|---|---|---|
| | SOLVENT | COMPOUND OF EXAMPLE 1 $10^{-5}$ M | COMPOUND OF EXAMPLE 17 $10^{-5}$ M |
| % CONTRACTION | | | |
| 5 MIN | 227.4 ± 30.6 | 158 ± 11 | 218.8 ± 50.8 |
| 15 MIN | 30.4 ± 3.7 | 60.5 ± 13 | 181 ± 51 |
| 60 MIN | 28.9 ± 5.3 | 20.5 ± 4.6 | 157.1 ± 42.6 |
| CONTRACTURE (%) | | | |
| 15 MIN | 42.7 ± 9.7 | 23.5 ± 6.2 | 0 |
| 30 MIN | 81.7 ± 13.4 | 52.2 ± 4.7 | 0 |
| 60 MIN | 44.9 ± 8.3 | 60.7 ± 4.4 | 0 |

These pharmacological tests show that the compounds of the present invention substantially prevent the development of the contracture and the collapse of the contraction linked to the toxic effects of ouabain and veratridine.

Thus, after 30 minutes' intoxication with ouabain, the contracture of guinea pig auricles is not significant in the presence of the compounds of the invention, whereas it exceeds 50% of the contraction developed in their absence. At the same time, the contractility is preserved in the presence of the compounds of the invention whereas it is reduced by 70% in the control experiments.

b) Protective effect of the compounds of the invention on an isolated heart subjected to an ischemia-reperfusion sequence.

Study procedure

The heart is removed from WISTAR rats (325-375 g). The heart is rapidly perfused according to the technique of LANGENDORFF at a constant pressure of $101.310^2$ Pa and electrically stimulated at 5 Hz.

The heart is subjected to a 30 min ischemia (produced by complete stoppage of the perfusion) followed by a 60 min reperfusion. The test compounds are incubated for 15 min before the ischemia.

Isovolumetric contractions are recorded by means of a polyethylene ballonet linked to a pressure sensor (P23-GOULD) introduced into the left ventricle and inflated so as to obtain a diastolic pressure of between $6.710^2$ and $13.310^2$ Pa.

Results

The compounds of the invention limit the development of contracture during the ischemic period and permit a better functional recuperation during reperfusion.

By way of example, the compound of Example 1 makes it possible, at a concentration of $810^{-7}$ M, to reduce by 47% relative to the control experiments the contracture developed after 30 minutes of ischemia and to improve the functional recuperation of the hearts by 55% relative to the control experiments at the end of the 60 minutes of reperfusion.

c) Protective effect of the compounds of the invention on an isolated heart subjected to hypoxia-reoxygenation.

An experimental procedure similar to that described in the preceding test is followed, the ischemia-reperfusion stage being replaced by a 60 min hypoxia produced by the administration of a 95% $N_2$ + 5% $CO_2$ gaseous mixture during this period and followed by a 30 min reoxygenation.

The test compounds are incubated for 15 min before and during the period of hypoxia.

Results

The compounds of the present invention also limit, under these conditions, the development of contracture during hypoxia and permit a better functional recuperation during reoxygenation. Thus, the compound of Example 17 reduces the contracture developed during control experiments by 42% and increases the contraction by more than 100% relative to the control hearts, after 30 minutes of reoxygenation.

CONCLUSION

These studies on myocardial tissue therefore show that the compounds of the present invention possess a potent protective effect as is shown with respect to an excess of intracellular calcium (ouabain or veratridine intoxication) or with respect to aggressions such as ischemia-reperfusion or hypoxiareoxygenation.

II IN VIVO STUDY

Studies were carried out in vivo in order to assess the antivasoconstrictive and protective activity of the compounds of the present invention towards aggression of the myocardium and to demonstrate their protective effect towards vascular lesions of a proliferative nature.

A/ Effect of the compounds of the invention on cardiovascular reactivity a) Effects of the compounds of the invention, administered intravenously, on cardiovascular reactivity to various vasopressors.

Study procedure

After a 30 to 60 min period of stabilization of wakeful WISTAR rats, a range of concentrations of phenylephrine (between 0 and 16 μg/kg) is injected intravenously.

Reading of the mean blood pressure and heart rate is carried out at the point where the pressor effect reaches its maximum. After a washing time of at least 2 hours, the test compound is administered intravenously (10 mg/kg) followed 15 minutes later by a new range of phenylephrine.

The same procedure is used to study the compounds of the invention for the pressor effects induced by angiotensin II (0 to 200 ng/kg) and vasopressin (0 to 200 ng/kg). These studies are carried out on different groups of animals.

Results

The compounds of the present invention very substantially reduce the pressure responses induced by the various vasopressors used.

By way of example, the compound of Example 17 reduces the pressure effect of phenylephrine by 81% when it is administered intravenously at a dose of 10 mg/kg.

b) Effects of the compounds of the invention, administered orally, on the cardiovascular reactivity of phenylephrine.

Study procedure

The procedure is carried out as above but the intravenous administration of the test compounds is replaced by oral administration (5, 10 and 20 mg/kg) of the test compound. The phenylephrine range is repeated 0.5, 1, 2, 3, 4, 5 and 6 hours after administration of the compound.

Results

After oral administration of the compounds of the invention, the pressor response is substantially reduced relative to the control group. Analysis of the various study times shows that the compounds of the invention have a good activity when administered orally and a long duration of action.

By way of example, the inhibitory activity of the compound of Example 17 appears 30 min after its administration, reaches its maximum after 2 hours (60% reduction of the vasopressor effect of phenylephrine at a dose of 20 mg/kg), and remains stable for 6 hours.

B/ Study of the hemodynamic action of the compounds of the present invention in rats.

Study procedure

After anesthesia with pentobarbital (60 mg/kg intraperitoneally), the animals are instrumented for the purpose of measuring the blood pressure, the heart rate and the renal, mesenteric and muscular blood flow rates. The rats are artificially ventilated at 50 cycles/min. After a stabilization period, cumulative doses of the test compounds are administered intravenously at 15 min intervals.

Results

The antivasoconstrictve activity of the compounds of the invention leads to a decrease in blood pressure linked to a peripheral vasodilatation and a reduction in the heart rate in these animals, whose sympathetic tonus is increased by the anesthetic procedure.

C/ Action of the compounds of the invention on reperfusion arrhythmias.

Study procedure

A thoracotomy and a coronary ligature are carried out on WISTAR rats. After stabilization for 10 min, 2 mg/kg of the test compound are administered intravenously. The blood pressure, the heart rate and the electrocardiogram are recorded. Five minutes after injecting the product, the coronary ligature is tightened.

The myocardial ischemia induced by this complete stenosis is revealed by a decrease in blood pressure and a rise in the ST segment of the electrocardiogram. After 5 minutes of stenosis, the ligature is removed and the electrocardiogram as well as the blood pressure are recorded for 10 consecutive minutes. The delay in the appearance of the various rhythm disorders as well as the mortality are measured.

Results

Reperfusion of the heart area that has been rendered ischemic very rapidly gives rise to the appearance of rhythm disorders: ventricular extrasystoles, ventricular tachycardias and ventricular fibrillations which may lead to the death of the animal (4 deaths out of 9 in the control group).

The compounds of the invention exhibit a very good protective effect against disorders of the reperfusion rhythm. By way of example, the intravenous injection of the compound of Example 17 very substantially delays the appearance of ventricular extrasystoles and tachycardias.

In animals treated with the compound of Example 17, the mortality rate is zero and the appearance of ventricular fibrillations is prevented to an extent of 100%.

D/ Effect of the compounds of the invention on the proliferation rate after endothelial denudation.

Study procedure 300-g male WISTAR rats are pretreated daily for 6 days with 10 mg/kg of the test compound administered orally. After pretreatment for 6 days (J6), denudation of the aortic endothelium of the animals is performed according to the following method:

After anesthetizing the animal with methohexital (Brietal, 60 mg/kg intraperitoneally), an embolectomy probe (Fogarty 2F) is introduced into the aorta through the left carotid.

Aortic deendothelialization is achieved by three successive passages of the probe.

Three days after the endothelial denudation (J9), the rats are sacrificed and the aorta is removed, incubated in a physiological solution for 1 hour at 37° C., and then transferred into a $^3$H-thymidine-enriched Krebs-Henseleit solution (specific activity: 1.48–2.22 TBq/moles) for 1 hour at 37° C. This is followed by a one-hour post-incubation in a Krebs-Henseleit solution lacking $^3$H-thymidine.

After washing in a Tris-EDTA buffer, the proliferation rate is calculated from the incorporation of 3H-thymidine.

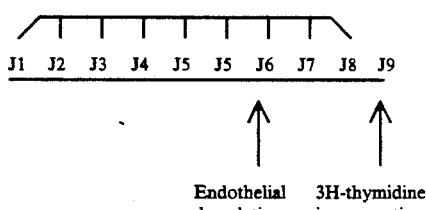

Oral administration of the compounds of the invention or of the vehicle

Endothelial denudation    3H-thymidine incorporation

Results

The compounds of the present invention substantially reduce the proliferation rate of smooth muscle cells of the aorta of rats which has undergone an endothelial denudation.

By way of example, the compounds of Examples 1 and 17 reduce the proliferation of smooth muscle cells by 40% when administered orally.

CONCLUSION

The studies carried out in vivo confirm the remarkable antivasoconstrictive and antiischemic activities of the compounds of the present invention and demonstrate a high protective effect towards the vascular smooth muscle cell proliferation process which constitutes an essential stage in the development of vascular lesions and in particular of atheromatous lesions and restenoses after vascular clearing.

We claim:

1. A compound selected from those of formula (I):

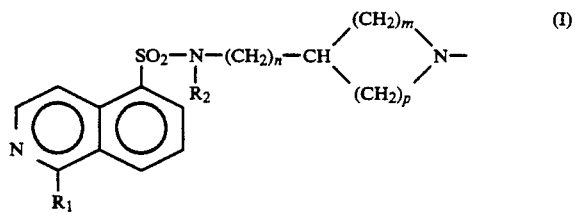

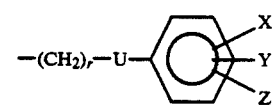

in which:

n is 0 or 1 to 4 inclusive, m and p are 1 to 4 inclusive, it being understood that the sum m+p is 2, 3, 4 or 5, r is 1 to 6 inclusive, $R_1$ represents hydrogen, chlorine, or hydroxy, $R_2$ represents hydrogen, lower alkyl, lower alkenyl, lower alkynyl, cycloalkyl, lower cycloalkylalkyl, phenyl, or phenyl loweralkyl, X, Y or Z, which are identical or different, represent hydrogen, halogen, or a group chosen from lower alkyl, lower alkoxy, nitro, amino, cyano, acetamido, carboxamido, or X and Y, or Y and Z, together form, with the 2 carbon atoms of the phenyl nucleus carrying them, a furan, dihydrofuran, or benzene ring, U represents a single bond, oxygen, sulfur, or a group chosen from: carbonyl, sulfinyl, sulfonyl, —NH—CO—, —CO—NH—, or —O—(CH$_2$)$_{r'}$—O—, with r' meaning 2 or 3, —(CH$_2$)$_{r''}$—O—(CH$_2$)$_{r'''}$— with r" and r''' meaning 1 or 2, and

where
R$_3$ represents:
- hydrogen,
- formyl,
- —A, —CO—A, or —CO—O—A, with A meaning lower alkyl, lower alkenyl, lower alkynyl, cycloalkyl, or cycloalkylloweralkyl,
- —(CH$_2$)$_q$-phenyl or substituted —(CH$_2$)$_q$— phenyl, with q meaning 0 or 1 to 4 inclusive,
- —CO—phenyl or substituted —CO—phenyl,
- —CO—O—phenyl or substituted —CO—O—phenyl,
- —CO—NR$_4$R$_5$ where
R$_4$ and R$_5$: - which are identical or different, represent hydrogen or a group chosen from lower alkyl, lower alkenyl, lower alkynyl, phenyl or phenyloweralkyl,
- or form with the nitrogen atom carrying them a saturated ring with 4 to 7 members, 3 to 6 of which are carbon atoms, it being understood that the term "substituted" which applies to the groups —(CH$_2$)$_q$—phenyl, —CO—phenyl, or —CO—O—phenyl means that these groups may be substituted by one or more radicals chosen from: lower alkyl, lower alkoxy, hydroxyl, a halogen atom, and trifluoromethyl, it being understood that the terms "lower alkyl" and "lower alkoxy" mean linear or branched saturated carbon groups having 1 to 6 carbon atoms, inclusive, that the terms "lower alkenyl" and "lower alkynyl" denote linear or branched unsaturated groups having 2 to 6 carbon atoms, inclusive,
- that the term "cycloalkyl" denotes a saturated carbon ring having 3 to 8 members, inclusive, the optical isomers thereof which may exist, as well as, where appropriate, its addition salts with a pharmaceutically-acceptable acid.

2. A compound of claim 1, in which m and p each represent 2, as well as, where appropriate, its addition salts with a pharmaceutically-acceptable acid.

3. A compound as claimed in claim 1, which is N-methyl-N-{1-[4-(p-fluorophenoxy)butyl]-4-piperidyl}-5-isoquinolinesulfonamide, as well as its addition salts with a pharmaceutically-acceptable acid.

4. A compound as claimed in claim 1, which is N-methyl-N-{[1-[3-(p-fluorophenoxy)propyl]-4-piperidyl]methyl}-5-isoquinolinesulfonamide, as well as its addition salts with a pharmaceutically-acceptable acid.

5. A compound as claimed in claim 1, which is N-methyl-N-{[1-[3-(p-fluorophenoxy)propyl]-3-pyrrolidinyl]methyl}-5-isoquinolinesulfonamide, its optical isomers, as well as its addition salts with a pharmaceutically-acceptable acid.

6. A compound as claimed in claim 1, which is N-{[1-[3-(p-fluorophenylamino)propyl]-4-piperidyl]methyl}-5-isoquinolinesulfonamide, as well as its addition salts with a pharmaceutically-acceptable acid.

7. A compound as claimed in claim 1, which is N-methyl-N-{[1-[4-(p-fluorophenyl)butyl]-4-piperidyl]methyl}-5-isoquinolinesulfonamide, as well as its addition salts with a pharmaceutically-acceptable acid.

8. A pharmaceutical composition useful for combating tissue pain containing, as active ingredient, an effective amount of at least one compound as claimed in claim 1, in combination with one or more pharmaceutically-acceptable excipients or vehicles.

9. A method for treating a living animal body afflicted with a condition due to or linked to tissue pain comprising the step of administering to the said body an amount of a compound of claim 1 which is effective for the alleviation of the said condition.

* * * * *

UNITED STATES PATENT AND TRADEMARK OFFICE
CERTIFICATE OF CORRECTION

PATENT NO. : 5,208,243

DATED : May 4, 1993

INVENTOR(S) : Jean-Louis Peglion, Jean-Paul Vilaine, Nicole Villeneuve, and Philip Janiak It is certified that error appears in the above-indentified patent and that said Letters Patent is hereby corrected as shown below:

| | |
|---|---|
| Col. 1, line 29: | "R$_H$" should read --R$_1$-- |
| Col. 1, line 49: | Insert the word --and-- |
| Col. 4, line 29: | "phenylor" should read --phenyl or-- |
| Col. 7, line 33: | "N-Methyl-N-{1-[4-(p" should read --N-Methyl-N-{1-[4-(p- -- |
| Col. 9, line 3 : | "mulitplets);" should read --multiplets);-- |
| Col. 9, line 24: | "N-Methyl-N-{1-[4-(phenoxy)butyl]4-piperidyl}-5" should read --N-Methyl-N-{1-[4-(phenoxy)butyl]-4-piperidyl}-5- -- |
| Col. 9, line 34: | "N-Methyl" should read --N-Methyl- -- |
| Col. 9, line 36: | "isoquinolinesultonamide" should read --isoquinolinesulfonamide-- |
| Col. 9, line 45: | "N-Methyl-N-{1-4-(1-naphthyloxy)" should read --N-Methyl-N-{1-[4-(1-naphthyloxy)-- |
| Col. 9, line 56: | "N-Methyl-N-{1-[4-(p-chlorophenoxy)butyl4-" should read --N-Methyl-N-{1-[4-(p-chlorophenoxy)butyl]4- -- |
| Col. 10, line 12: | "N-Methyl" should read --N-Methyl- -- |
| Col. 13, line 7 : | "N-{[1-[3" should read --N-{[1-[3- -- |
| Col. 13, line 32: | "[1-[4-(p-fluorophenyl)" should read --{1-[4-(p-fluorophenyl)-- |
| Col. 15, line 38: | "5-(p-Fuorophenoxy)" should read --5-(p-Fluorophenoxy)-- |
| Col. 15, line 63: | "1 Bromo-2-" should read --1-Bromo-2- -- |
| Col. 16, line 6 : | "ethyl]-4 piperi-" should read --ethyl]-4-piperi- -- |
| Col. 16, line 55: | "methylaine" should read --methylamine-- |
| Col. 25, line 8 : | "antivasoconstrictve" should read --antivasoconstrictive-- |
| Col. 26, line 12: | Delete the second "J5" in the graph |

Page 1 of 2

UNITED STATES PATENT AND TRADEMARK OFFICE
CERTIFICATE OF CORRECTION

PATENT NO. : 5,208,243
DATED : May 4, 1993
INVENTOR(S) : Jean-Louis Peglion, Jean-Paul Vilaine, NIcole Villeneuve, and Philip Janiak It is certified that error appears in the above-identified patent and that said Letters Patent is hereby corrected as shown below:

Col. 27, line 30: "pheny," should real --phenyl--.

Signed and Sealed this

Seventh Day of June, 1994

Attest:

BRUCE LEHMAN

Attesting Officer

Commissioner of Patents and Trademarks